(12) United States Patent
Medoff

(10) Patent No.: US 7,942,877 B2
(45) Date of Patent: May 17, 2011

(54) GUIDE SYSTEM AND ASSOCIATED METHOD FOR INSTALLING AN IMPLANT DEVICE ADAPTED TO APPLY COMPRESSION ACROSS A FRACTURE SITE

(76) Inventor: Robert J. Medoff, Kailua, HI (US)

( * ) Notice: Subject to any disclaimer, the term of this patent is extended or adjusted under 35 U.S.C. 154(b) by 215 days.

(21) Appl. No.: 12/265,972

(22) Filed: Nov. 6, 2008

(65) Prior Publication Data

US 2009/0131937 A1    May 21, 2009

Related U.S. Application Data

(63) Continuation-in-part of application No. 11/377,605, filed on Mar. 16, 2006, which is a continuation-in-part of application No. 10/073,826, filed on Feb. 11, 2002, now Pat. No. 7,037,308.

(60) Provisional application No. 60/268,099, filed on Feb. 12, 2001.

(51) Int. Cl.
*A61B 17/56* (2006.01)

(52) U.S. Cl. .............. 606/64; 606/103; 606/324
(58) Field of Classification Search .............. 606/324, 606/71, 281, 309, 280, 286, 151, 64, 103, 606/65, 70; 128/898
See application file for complete search history.

(56) References Cited

U.S. PATENT DOCUMENTS

| 5,658,283 | A | * | 8/1997 | Huebner | 606/57 |
| 5,899,906 | A | * | 5/1999 | Schenk | 606/301 |
| 7,713,271 | B2 | * | 5/2010 | Warburton | 606/64 |

FOREIGN PATENT DOCUMENTS

FR    EP0693272    *    1/1996    ............. 606/64

* cited by examiner

Primary Examiner — Pedro Philogene
(74) Attorney, Agent, or Firm — Ladas & Parry

(57) ABSTRACT

An implant for fracture fixation in which a wire element has one end installed in bone and an opposite end fixed externally to the bone to apply compression across the fracture wherein a guide system is provided for guiding a tip of the one end of the wire element into a pilot hole in the bone prior to producing compression across the fracture.

14 Claims, 15 Drawing Sheets

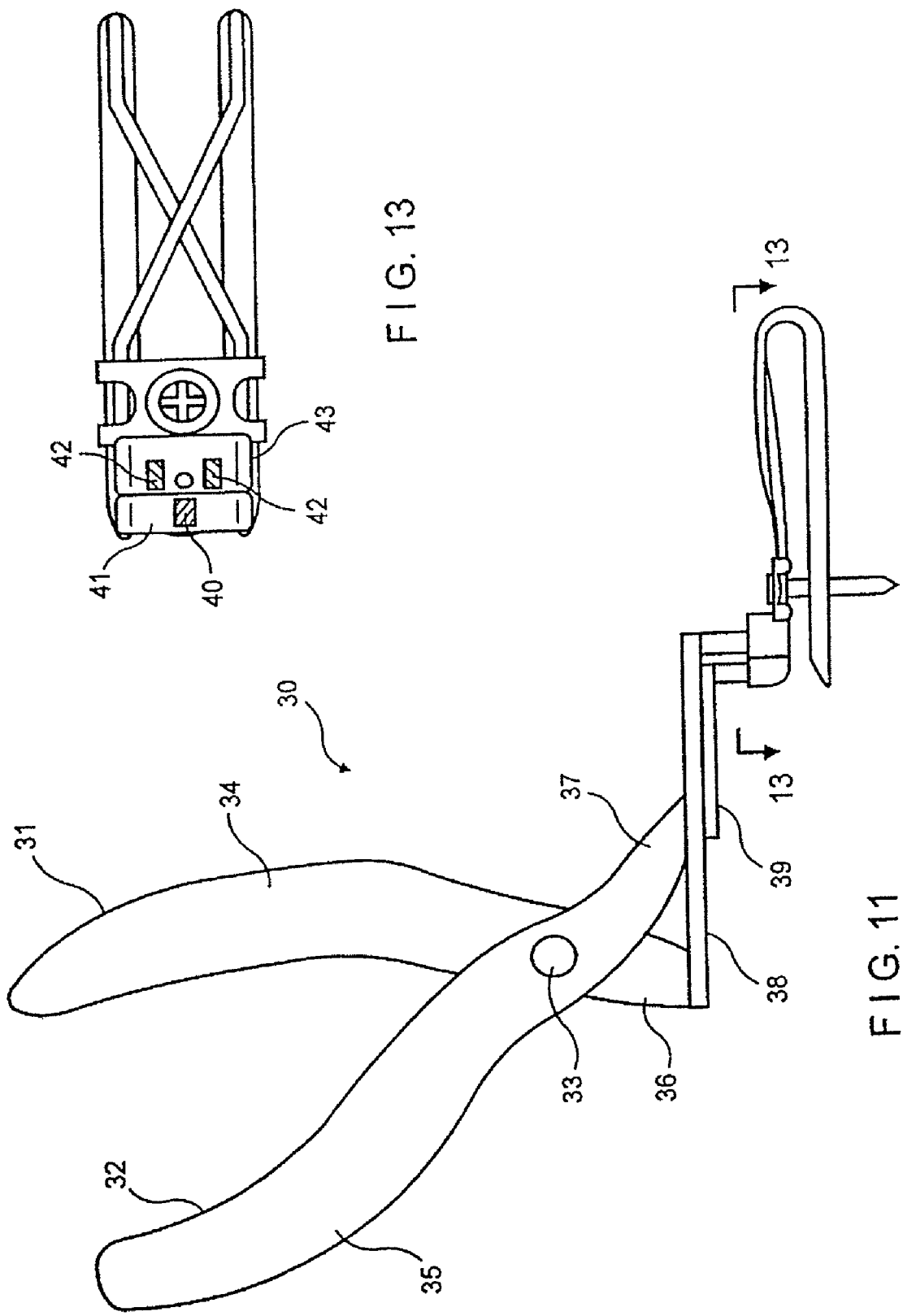

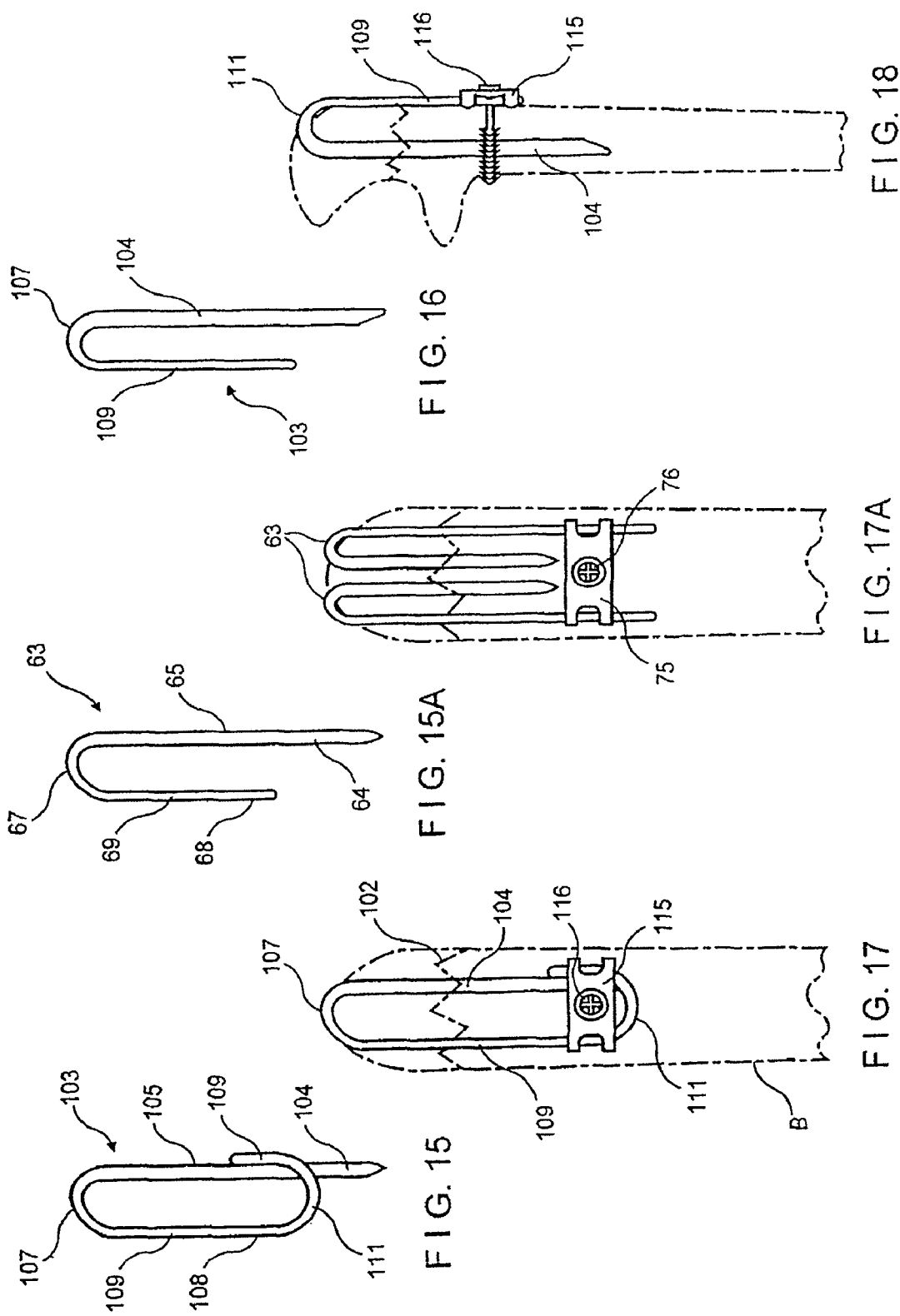

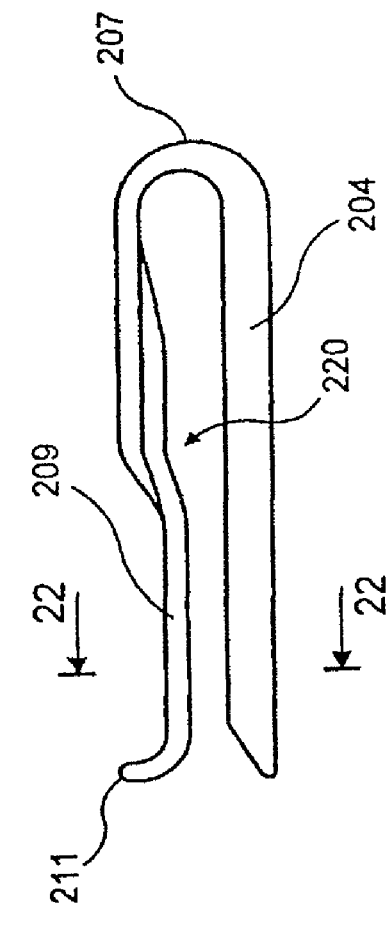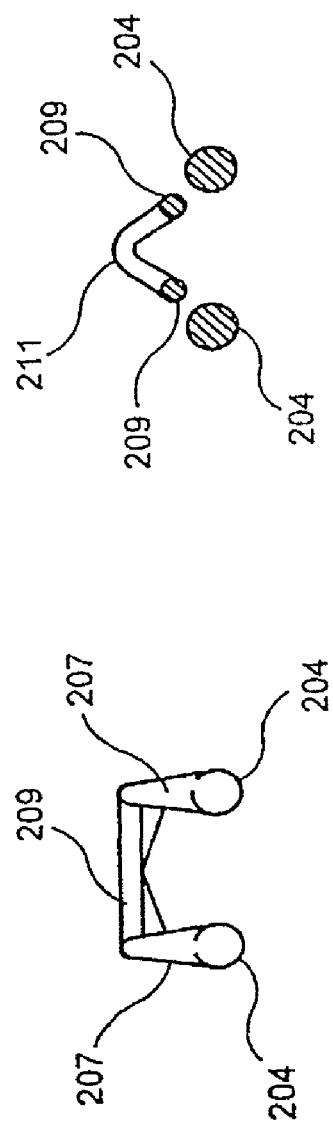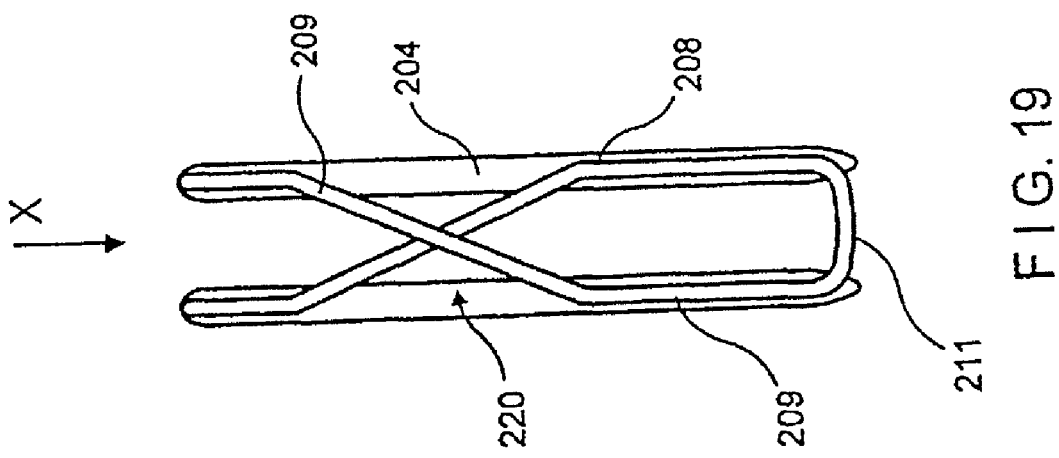

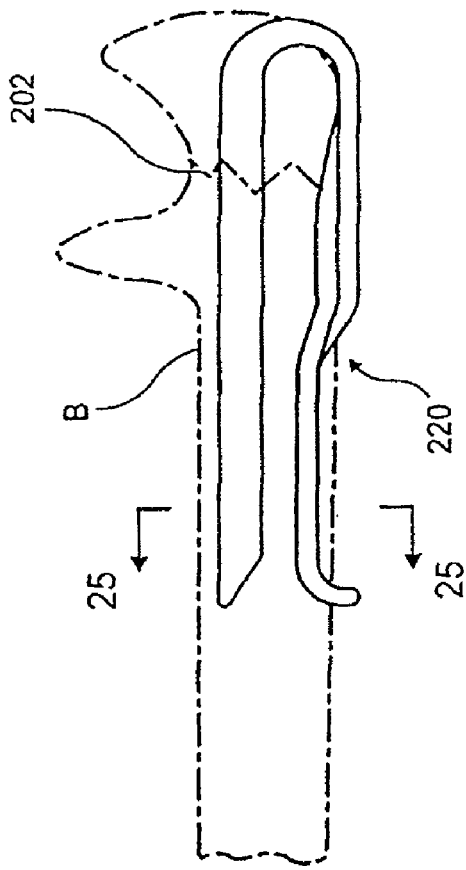
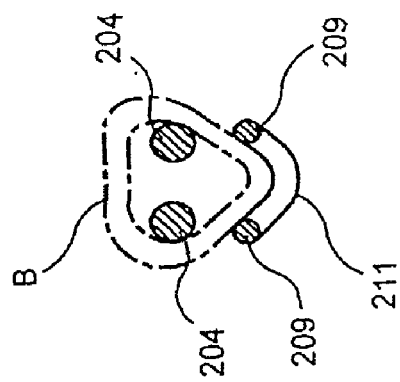
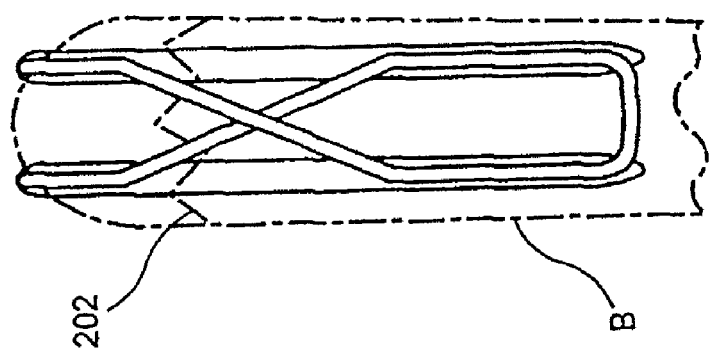

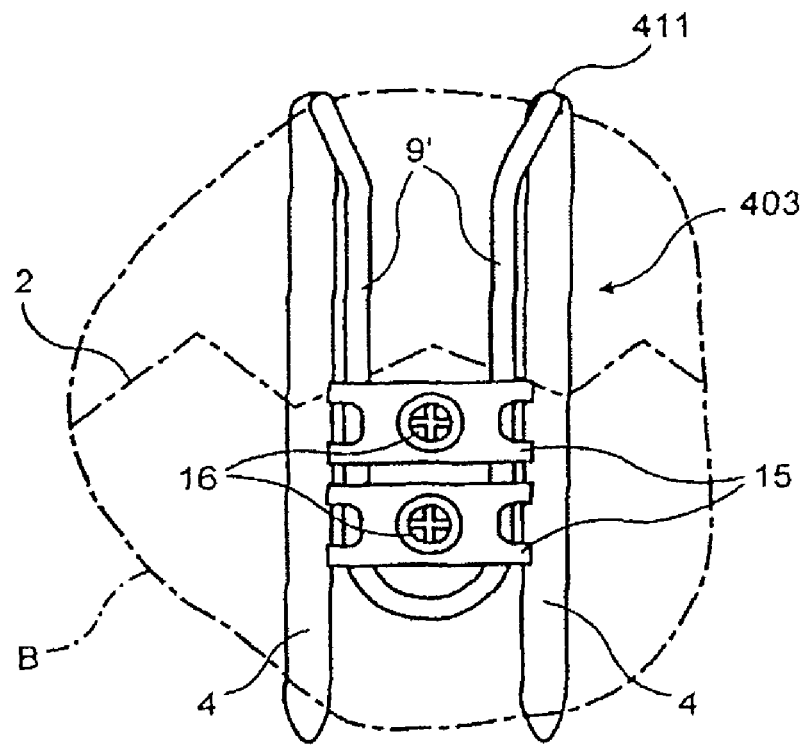
F I G. 30
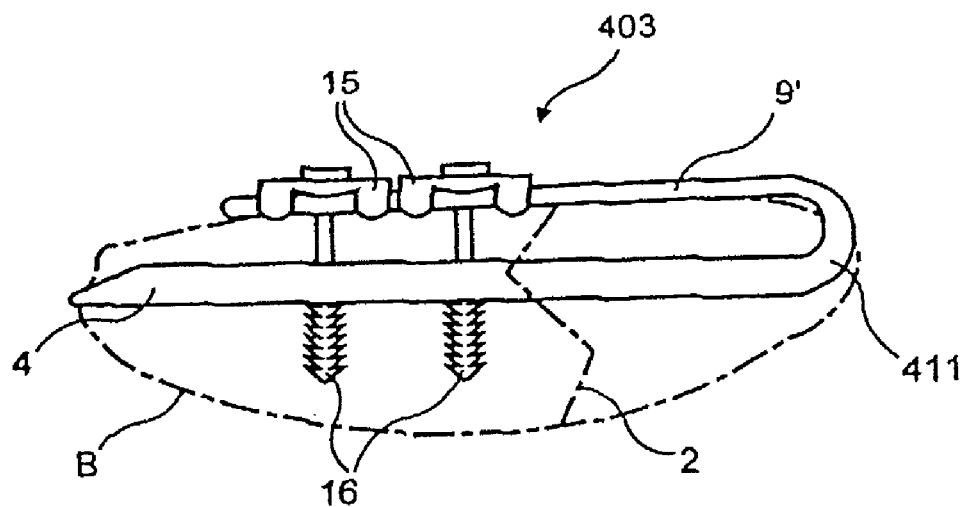
F I G. 31

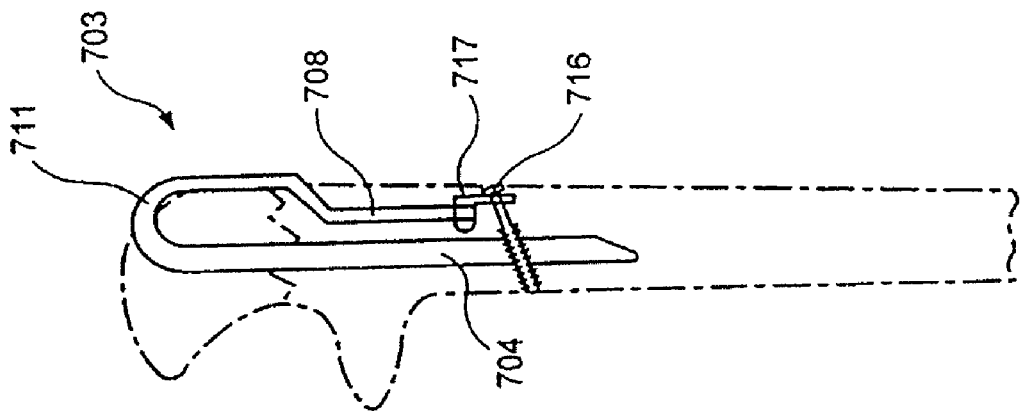
FIG. 41
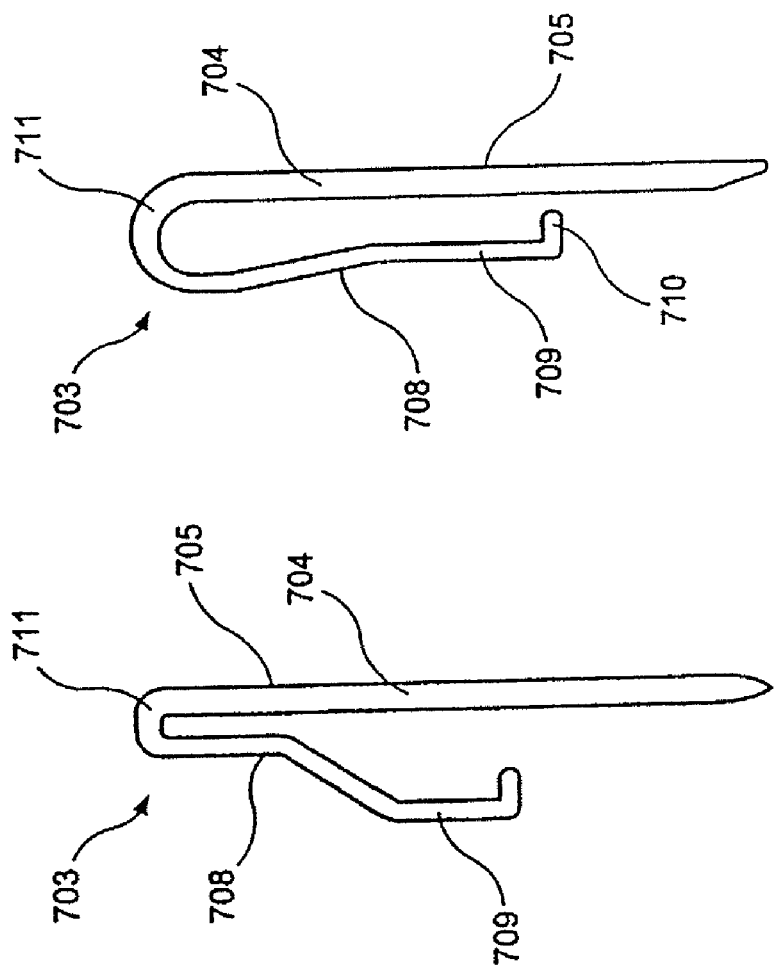
FIG. 37
FIG. 36

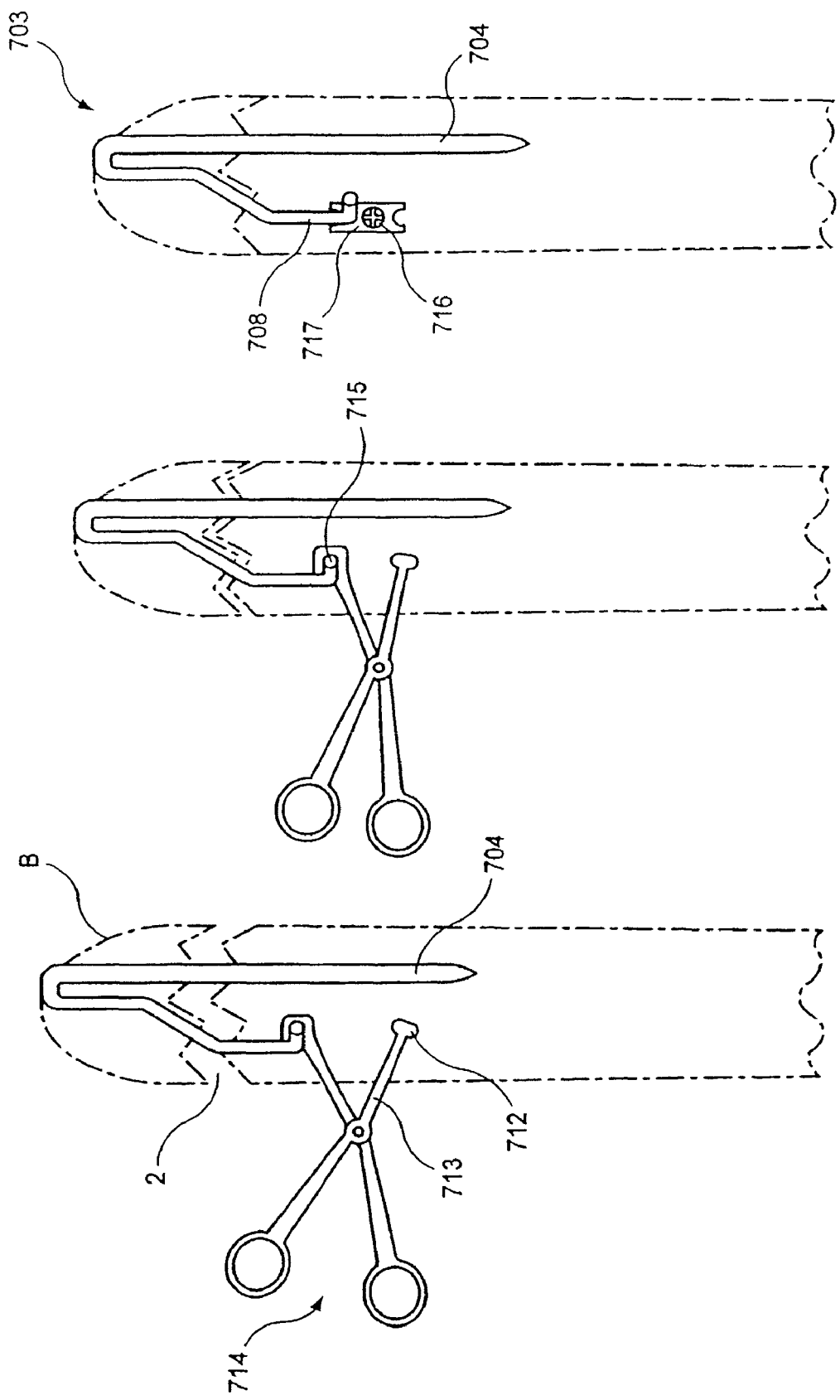

GUIDE SYSTEM AND ASSOCIATED METHOD FOR INSTALLING AN IMPLANT DEVICE ADAPTED TO APPLY COMPRESSION ACROSS A FRACTURE SITE

CROSS RELATED APPLICATION

This application is a C-I-P of application Ser. No. 11/377,605 filed Mar. 16, 2006 which in turn is a C-I-P of application Ser. No. 10/073,826 filed Feb. 11, 2002 (now U.S. Pat. No. 7,037,308) which claims the priority of Provisional Application Ser. No. 60/268,099 filed Feb. 12, 2001.

FIELD OF THE INVENTION

The invention relates to an implant device for applying compression across a fracture site in a bone and more particularly to a guide means and associated method for installing the implant device in bone.

BACKGROUND AND PRIOR ART

By way of example, fractures of the olecranon (upper end of the ulna at the level of the elbow), fractures of the medial malleolus (ankle), and fractures of the patella (kneecap) are fractures that involve an articular surface. Restoration of the joint surface to anatomic alignment is the accepted method of fixation.

Both the olecranon and patella are loaded during joint flexion. The deep articular surface is loaded in longitudinal compression by the reactive forces across the articular surface; the superficial bone surface is loaded in tension by the pull of a strong muscular insertion (the triceps in the case of the olecranon, and the quadriceps tendon in the case of the patella). As a result, these bones normally have a compressive side (deep surface) and a tension side (superficial surface).

A well accepted method of fixation of both olecranon fractures and patella fractures is a technique known as FIG. 8 tension band wiring. FIGS. 1 and 2 show an example of the known technique. Referring to these figures, two stiff stainless steel pins A are driven longitudinally into bone B across the fracture site C. Instead of pins, screws can be utilized. A flexible wire D is passed through a drill hole E on one side of the fracture site C and the two ends of the wire are crossed over the fracture site to the opposite side. One wire is then passed under the ends F of the two pins A, and the wire twisted and tightened at G to the other end to develop tension in the wire to produce compression across the fracture site.

The tension band technique holds the tension side of the bone in apposition. Since the deep surface is under load from the articular surface, the technique results in production of compressive force across the fracture site, resulting in secure fixation, promoting early union of the fracture and early motion of the joint.

One problem with this standard FIG. 8 tension band wiring occurs because standard large pins A are used which protrude from the end of the bone at F at the location where a major tendon inserts. Because of this, the ends F of the pins frequently cause irritation of the soft tissues and require removal.

A minor technical problem with the standard FIG. 8 tension band wiring is that the passage of the wire through drill hole D and through the tendon and under the pins can be cumbersome.

SUMMARY OF THE INVENTION

The invention provides an implant for fracture fixation in which a wire element has one end installed in bone and an opposite end fixed externally to the bone to apply compression across the fracture wherein a guide means is provided for guiding a tip of said one end of the wire element into a pilot hole in the bone.

BRIEF DESCRIPTION OF THE FIGURES OF THE DRAWING

FIG. 11 is an elevational view of a different embodiment of the tensioning device in a relaxed state.

FIG. 13 is a sectional view taken along line 13-13 in FIG. 11.

FIG. 15 is a plan view illustrating a further embodiment of the invention.

FIG. 15A is a plan view of a modification of the embodiment illustrated in FIG. 15.

FIG. 16 is a side elevational view of the embodiment illustrated in FIG. 15.

FIG. 17 is a top plan view showing the embodiment of FIG. 15 installed in the bone.

FIG. 17A is similar to FIG. 17 but illustrates the modification in FIG. 15A.

FIG. 18 is a side elevational view showing the embodiment of FIG. 15 installed in the bone.

FIG. 19 is a top plan view of a further embodiment of the invention.

FIG. 20 is a side elevational view of the embodiment in FIG. 19.

FIG. 21 is an end view as seen in the direction of arrow X in FIG. 19.

FIG. 22 is a sectional view taking on line 22-22 in FIG. 20.

FIG. 23 is a side elevational view showing the embodiment of FIG. 19 installed in the bone.

FIG. 24 is a top plan view of FIG. 23.

FIG. 25 is a sectional view taking along line 25-25 in FIG. 23.

FIG. 30 is a plan view of a further embodiment of the invention shown installed in the bone.

FIG. 31 is an elevational view of FIG. 30.

FIG. 36 is a top plan view of another embodiment of a fixation device according to the invention.

FIG. 37 is a side elevational view thereof.

FIGS. 38 and 39 illustrate successive stages of installation of the fixation device of FIG. 36.

FIG. 40 shows the installation of the fixation device in top plan view.

FIG. 41 shows the installation of the fixation device in side elevation view.

DETAILED DESCRIPTION

The drawings illustrate a fracture fixation implant device 1 for applying compression across a fracture 2 in a bone B. The bone B, for example, may be the olecranon or the patella that involve an articular surface.

Figure 1:
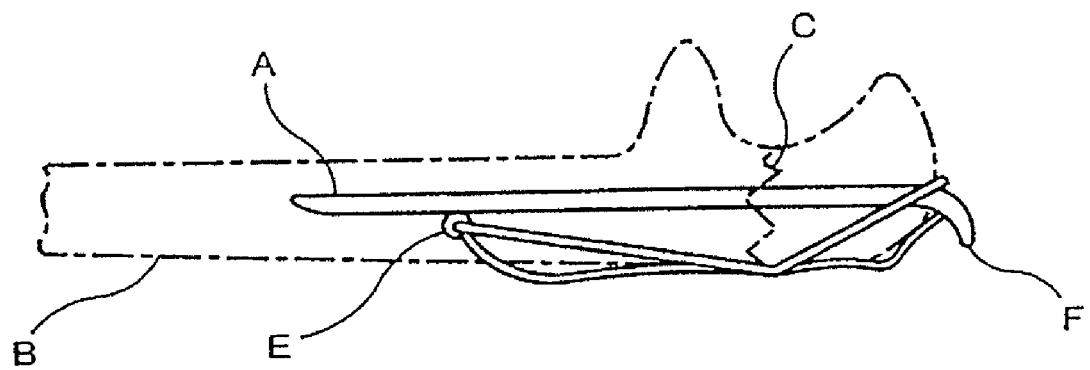
FIG. 1 is a side view of a conventional fixation device.
Figure 2:
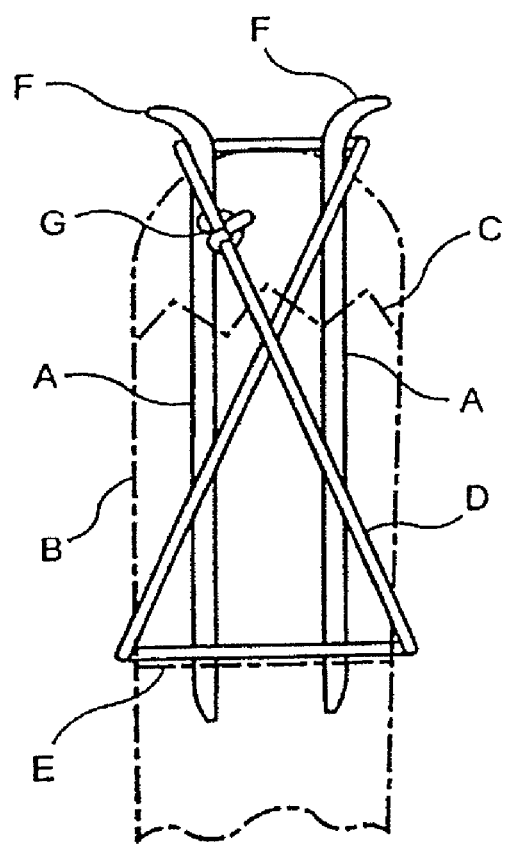
FIG. 2 is a plan view, from below at the posterior side in FIG. 1.
Figure 3:
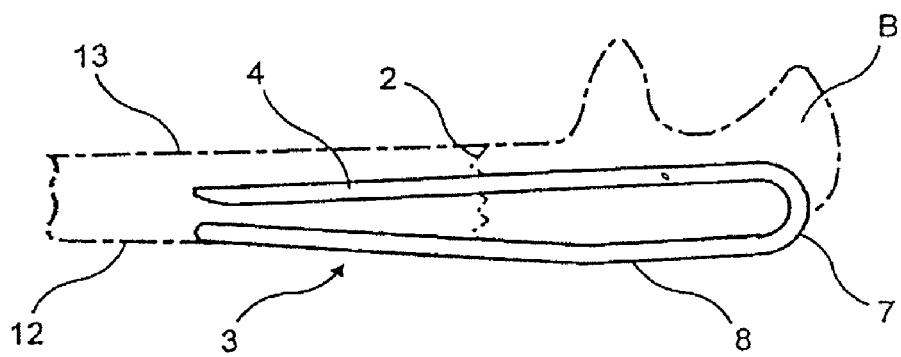
FIG. 3 is a side view of the fixation device of the invention implanted in a bone.

The implant device 1 comprises a continuous wire element 3 formed with two spaced longitudinally extending legs 4 which are adapted to be driven into the bone B across the fracture 2. The term "wire" or "wire element" is an art recognized term and covers elements having circular or rectangular cross-sections and commonly referred to as pins, wires or bars. The legs 4 form a first portion 5 of the wire element and the legs 4 extend at their ends remote from free ends 6 thereof to bend portions 7 extending outside the bone. Integrally connected to bend portions 7 is a second portion 8 extending backwardly from the bend portions 7 in juxtaposition with the legs 4 of the first portion 5. The second portion 8 includes legs 9 continuous with respective bend portions 7 and crossing one another at an intersection 10 which is located approximately at the fracture 2. The legs 9 extend to a connecting portion 11 in the form of a U-shaped bend to complete the continuity of the wire element 3. In FIG. 3 the wire element 3 is illustrated in an embedded condition in the bone so that the second portion 8 extends on a lower or posterior surface 12 of the bone.

Figure 4:
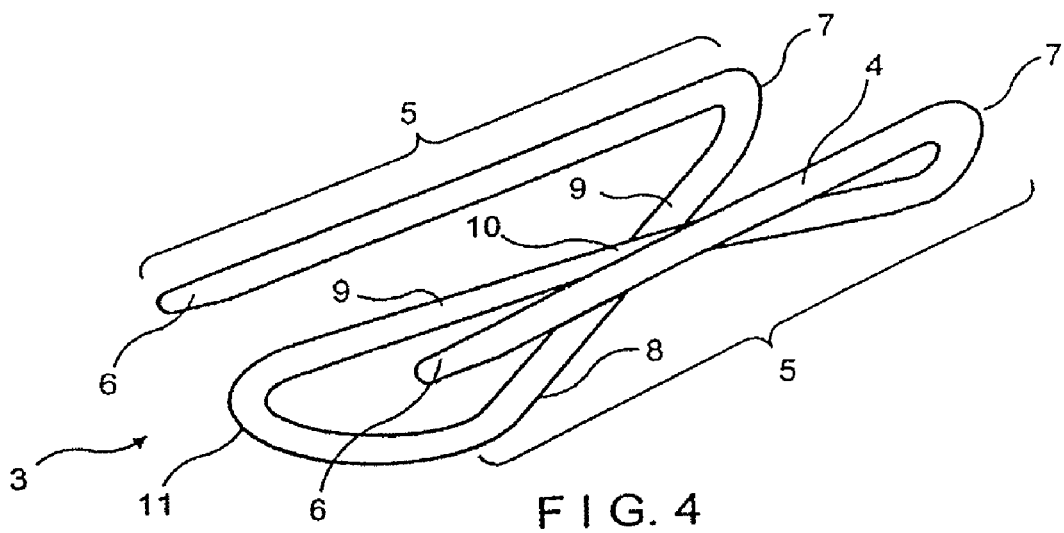
FIG. 4 is a perspective view of one embodiment of the fixation device.
Figure 4A:
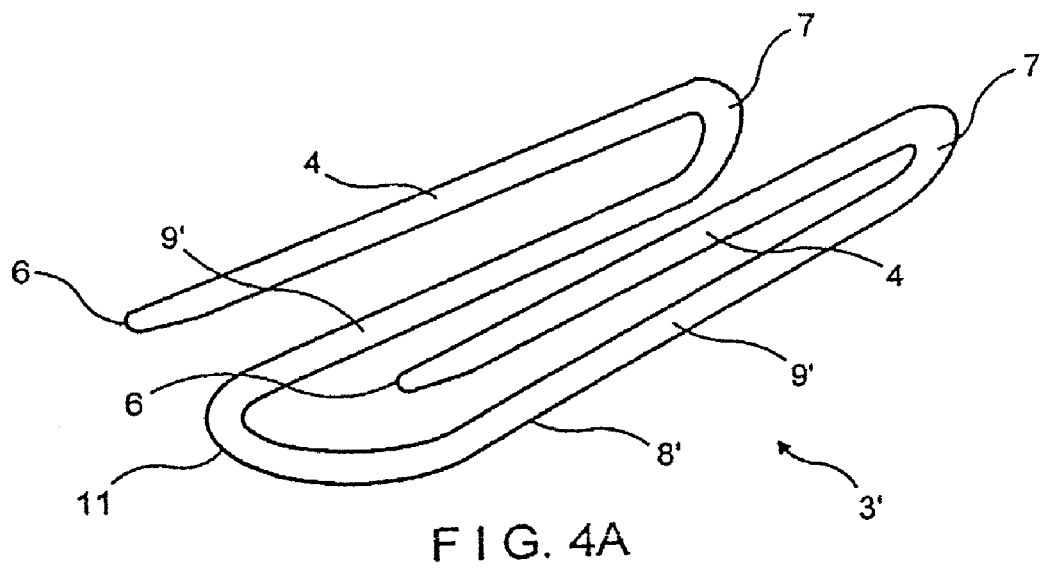
FIG. 4A is a perspective view of another embodiment of the fixation device.

FIG. 4A illustrates a modified embodiment of the wire element in which the same numerals are used to designate the same parts and primes are used for modified parts. In FIG. 4A, the wire element 3' has legs 9' of the second portion 8' which do not cross one another as in FIG. 4 but are spaced from one another. In other respects, the wire element 3' is the same as wire element 3 in FIG. 4.

Hereafter, the invention will be described with reference to the wire element 3 of FIG. 4, but it is to be understood that the wire element 3' could also be used.

Figure 6:
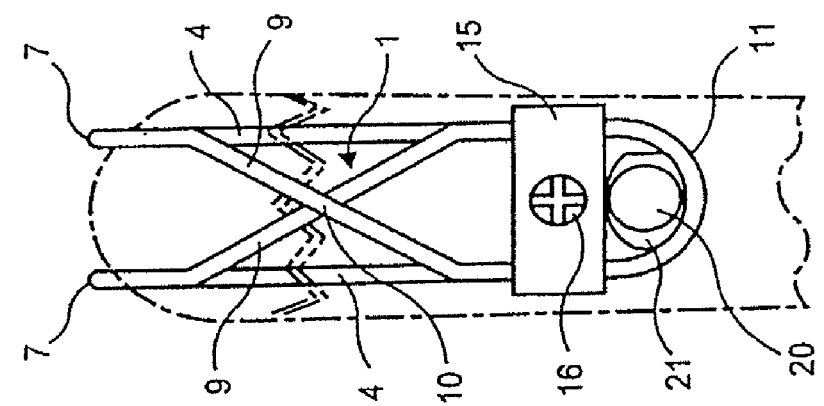
FIG. 6 shows the device of FIG. 5 with a tensioning device prior to application of tension force.
Figure 5:
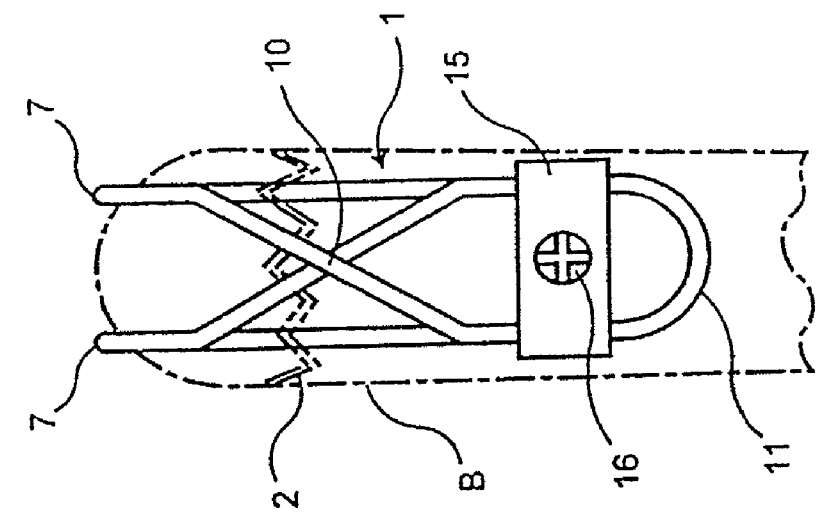
FIG. 5 is a plan view of the fixation device at the posterior side.

A washer 15 is secured at the posterior surface 12 of the bone by a bone screw 16. The legs 9 are loosely disposed below the washer 15. A tensioning device 20 is then installed between the washer 15 and the bend portion 11 of the wire element 3. The tensioning device 20 includes a rotatable cam 21 temporarily installed in the bone. In the position shown in FIG. 6, the cam does not apply any tension to the wire element

Figure 7:
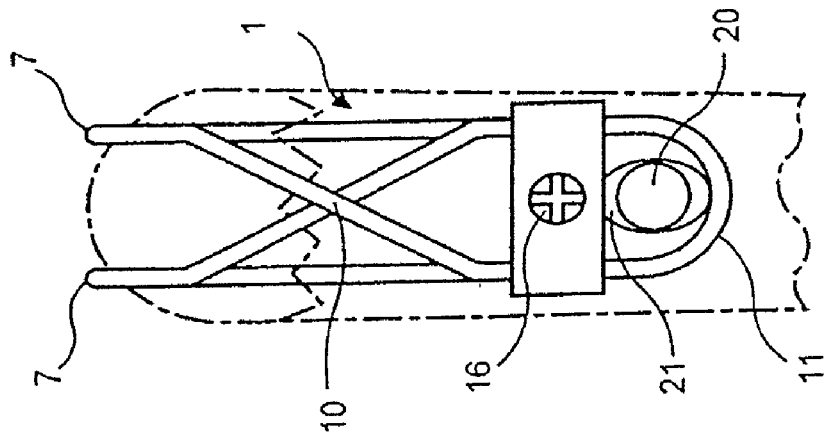
FIG. 7 shows application of tension force by the tensioning device.

3. When the cam is turned from the position shown in FIG. 6, a force is applied to the U-shaped bend 11 which develops tension in the wire element and causes the bend portions 7 to bear tightly against the distal end of the bone and produce compression across the fracture 2. In the ninety degree position shown in FIG. 7 of the cam 21, a maximum compression is developed across the fracture 2. When the proper tension has been developed in the wire element, the washer which has been loosely seated by the bone screw 16 is then fully seated by tightening the bone screw 16. Thereby, the tension in the wire element is maintained. The cam 21 which has been temporarily installed in the bone is then removed.

Figure 8:
FIG. 8 is a side view of a modified embodiment of the fixation device in which the wires are crossed at the upper or superior surface of the bone.
Figure 9:
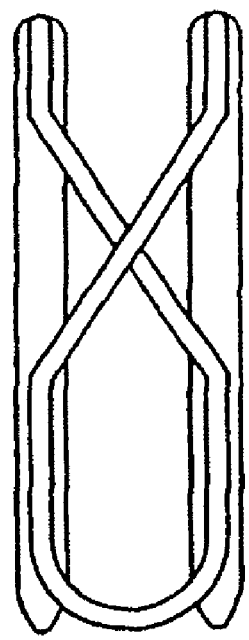
FIG. 9 is a top plan view of the device in FIG. 8.
Figure 10:
FIG. 10 is an end view of the device in FIG. 8.
Figure 14:
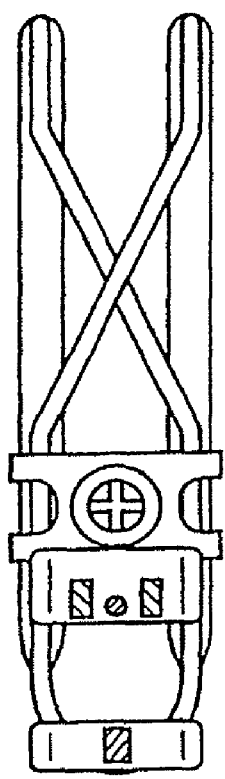
FIG. 14 is a sectional view taken along line 14-14 in FIG. 12.

FIGS. 8-10 are similar to the embodiment of FIGS. 3-7 except that the second portion 8 with the legs 9 or 9' is adapted to extend on the upper or anterior surface of the bone and tensioning of the wire element takes place at the upper surface. In practice, the legs 9 or 9' can be positioned on any superficial surface of the bone.

The installation of the implant is carried out as follows.

Two holes are drilled at the end of the bone at a spacing corresponding to the width of the implant as measured by the spacing of the legs 4 of the implant device thereof. The legs 4 of the implant device are impacted longitudinally into the drilled holes entering and aligning to the medullary canal. The fracture site is closed and the implant device is firmly seated and secured with the bone screw and washer to the bone at one end of the implant device. Compression at the fracture is achieved by turning the cam between the washer and the U-shaped bend of the implant device to effect further compression whereafter the screw is fully tightened and the washer is seated and then the cam is removed. In lieu of the cam, the tension force in the wire element can be produced by the surgeon applying pressure to the U-shaped bend portion 11 and then tightening the bone screw 16 while the wire is under tension.

Implant devices having wire elements of different diameter are suited for different bone fractures. For example, a 0.062 inch diameter wire can be used for olecranon fractures whereas a larger diameter wire would be used for patella fractures and a smaller diameter wire element may be used for transverse lateral or medial malleolar fractures.

In accordance with a particular feature of the invention, the diameter of the wire of the continuous wire element need not be uniform along its length and it is particularly advantageous if the legs 4 of the wire element are of greater diameter than the remainder of the wire element in the legs 9 or 9' and U-shaped bend 11 of the second portion 8 or 8'. In this way, absolute reliability of the embedded legs 4 of the first portion is obtained while flexibility of the wire element of the second portion can be obtained to achieve development of adequate tension in the wire element and resulting compression across the fracture. In addition, having a smaller diameter wire on the surface of the bone is less prominent and less likely to result in soft tissue irritation or inflammation.

Figure 12:
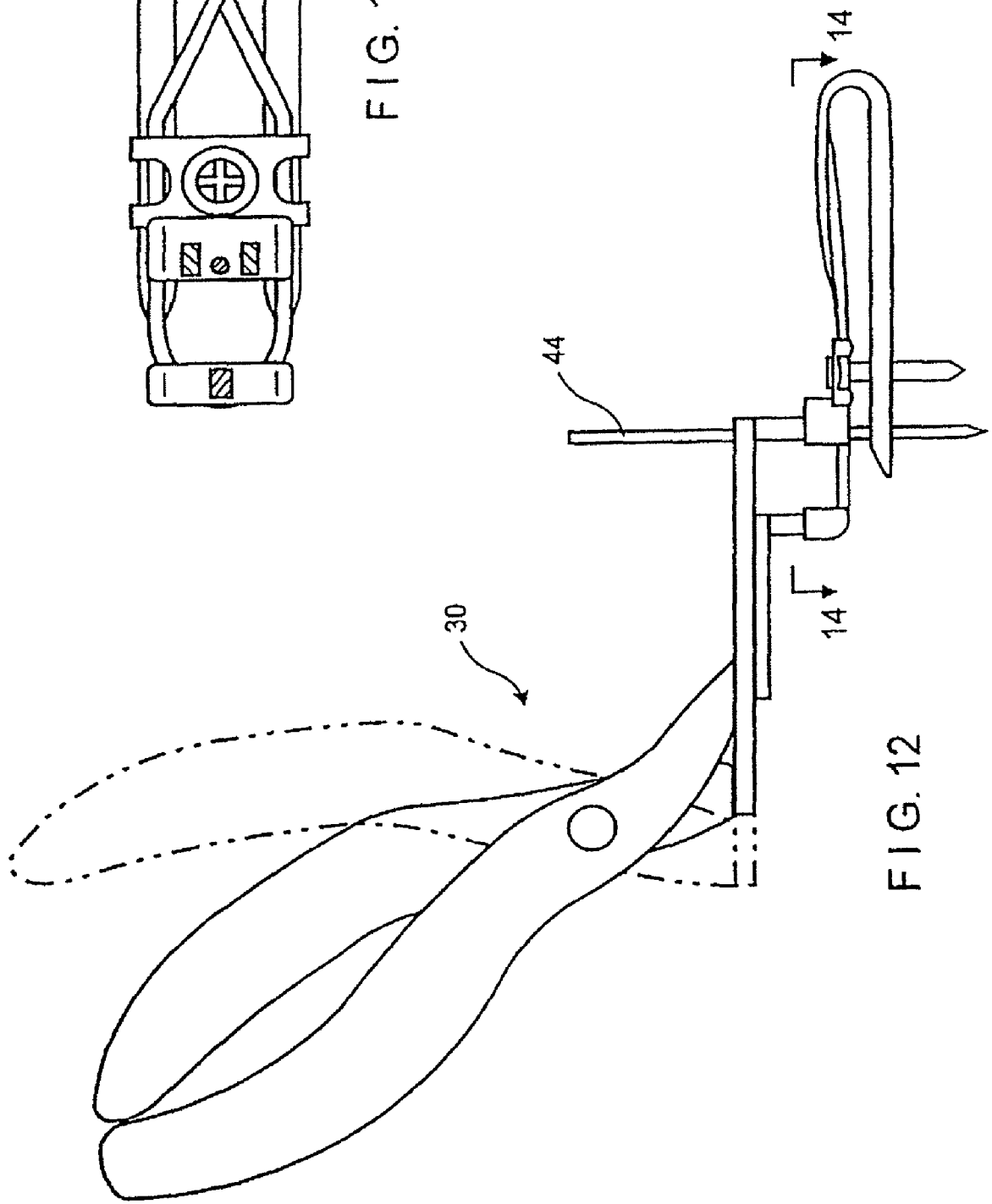
FIG. 12 shows the tensioning device of FIG. 11 in an active state in which tension is applied to the fixation device.

FIGS. 11-14 show another embodiment of the tensioning device designated generally by numeral 30. The tensioning device 30 comprises lever arms 31 and 32 connected together by a hinge 33. The arms 31 and 32 have respective hand-engaging gripper ends 34 and 35 above the hinge 33 and actuator arms 36 and 37 below hinge 33. The arm 36 supports an actuating jaw 38 at its lower end and the arm 37 supports a counter-bearing jaw 39 at its lower end. The jaws 38 and 39 are slidable with respect to one another and jaw 38 can be moved from an inactive state, as shown in FIG. 11 in which the wire element is not subjected to tensile stress by the tensioning device, to active state as shown in FIG. 12 in which the jaw 38 has been displaced to apply tension to the wire element. The jaw 39 is connected by a strut 40 to an actuator plate 41 and the jaw 38 is connected by struts 42 to a counter-bearing plate 43. The counter-bearing plate 43 can be secured by a temporary pin 44 which is placed in a drill hole in the bone. The U-shaped bend 11 of the second portion 8 of the wire element, passes around a back surface of the actuator plate 41. When the lever arms 34 and 35 are brought together as shown in FIG. 12, the actuator plate 41 is displaced away from the counter-bearing plate 43 to produce tension in the wire element. When the desired degree of tension has been achieved, the bone screw 16 is fully tightened, the pin 44 is extracted and the tensioning device is removed.

Although the prior figures have depicted an implant with two separate legs for both the first portion 5 and the second portion 8, either the first portion 5 or the second portion 8 or both may consist of one leg or more than two legs Referring to FIGS. 15 and 16, therein is shown a further embodiment of a fixation device 103 according to the invention in which the first portion consists of a single leg. The fixation device 103 has a leg 104 adapted for insertion into the bone and the leg 104 extends to a bend 107 connected to one leg 109 of the second portion 108 of the device. A U-shaped bend 111 connects leg 109 with a second leg 109 of the second portion 108. FIGS. 17 and 18 illustrate the installation of the fixation device 103 in bone B. As seen therein, the leg 104 is driven into the bone and extends across the fracture 102 and the second portion 108 consisting of legs 109 extends on an outer surface of the bone. The legs 109 of the second portion are secured to the bone by a bone screw 116 installed in a washer 115, following the development of tension in the device in a manner previously explained.

FIGS. 15A and 17A illustrate a modification of the embodiment illustrated in FIGS. 15 and 17. Herein, the fixation device is comprised of two parts 63 each having a leg 64 adapted to be implanted into the bone to form fixation portion 65. The leg 64 is connected by a bend 67 to second leg 69 of second portion 68 which extends backwardly and is juxtaposed with leg 64. The second legs 69 of the two parts 63 can be pulled to fix the fracture and develop tension in parts 63 and apply compression across the fracture. Washer 75 is secured to the bone by bone screw 76 to connect the second legs 69 together and maintain the tension developed in the two parts 63 via the second legs 69.

FIGS. 19 through 25 illustrate another embodiment of the fixation device according to the invention which is particularly applicable to the fixation of a fracture of the olecranon. This embodiment is distinguished from the earlier described embodiments in that the second portion 208 is non-planar but is bent in more than one plane to match the contour of the bone as shown with particularity in FIG. 25. In particular, the fixation device comprises two legs 204 which are driven into the intramedullary canal across the fracture 202. The legs 204 extend to the bend portions 207 which extend out of the bone to the second portion 208 which comprises the crossed legs 209 connected together by the U-shaped bend 211. It is noted that the U-shaped bend 211 is not composed only of curved portions but includes a straight portion with end radii connecting the U-shaped bend 211 to the legs 209 of the second portion 208. When reference is made in this disclosure to the U-shaped bend, this not only includes curved portions but portions which can be straight and includes such configurations as V-shaped bends and the like. The legs 209 of the second portion 208 have a transition region 220 in which the legs are bent out of plane and pass in opposition at the sides of the bone as shown in FIG. 25. The U-shaped bend 211 extends out of plane and connects the ends of the legs 209 as shown in FIGS. 22 and 25. The legs 204 are formed with a larger diameter than the legs 209 and there is a gradual taper in diameter between the legs at the bend portions 207. As evident from FIG. 25, the U-shaped bend 211 which is curved in two planes engages the surface of the bone B and forms a stabilized engagement therewith.

Figure 26:
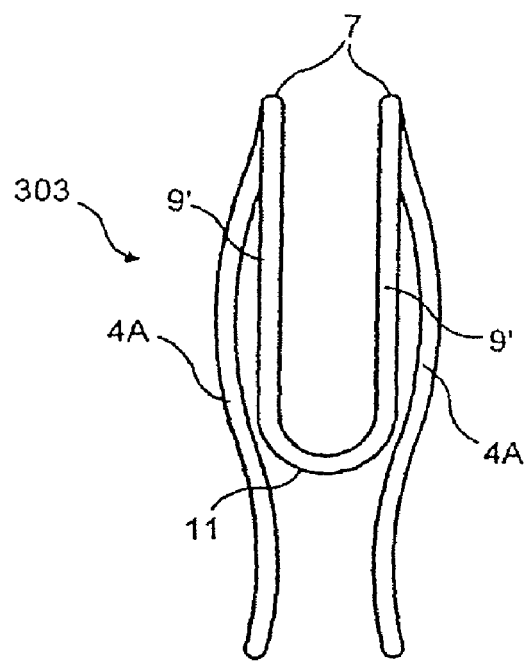
FIG. 26 is a plan view of a further embodiment according to the invention.
Figure 27:
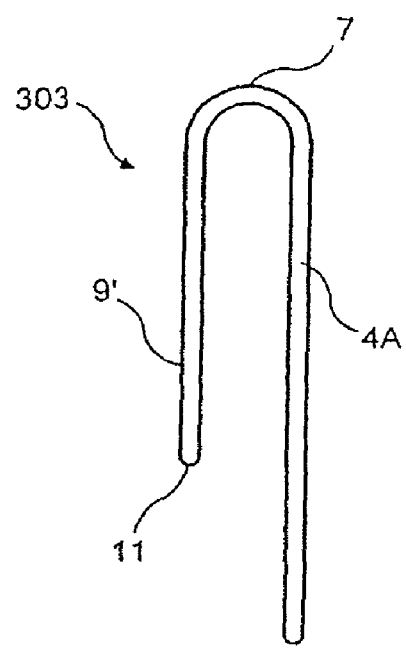
FIG. 27 is a side elevational view of the embodiment shown in FIG. 26.

FIGS. 26 and 27 show another embodiment of the fixation device designated 303 which is similar to the embodiment shown in FIG. 4A. The same reference numerals will be used to designate the same parts. The fixation device 303 is particularly applicable for fractures at the distal end of the ulna which is often fractured in addition to fractures of the distal radius. In this embodiment, the diameter of the wire elements is constant throughout and the characterizing feature is that the legs 4A which are inserted into the bone (the ulna) are not linear but have a curved or bent shape to produce a resilient effect when inserted into the intramedullary canal to produce greater fixation of the bone from the interior and help prevent the device from rotating due to resilient engagement of the legs 4A within the intramedullary canal. In use, the free ends of the legs 4A of the fixation device 303 are inserted into the intramedullary canal and squeezed together so that upon further insertion the more widely spaced bend portions of the legs 4A are squeeze more tightly and secure the fixation device with resilient pressure against the inner wall of the intramedullary canal.

Figure 28:
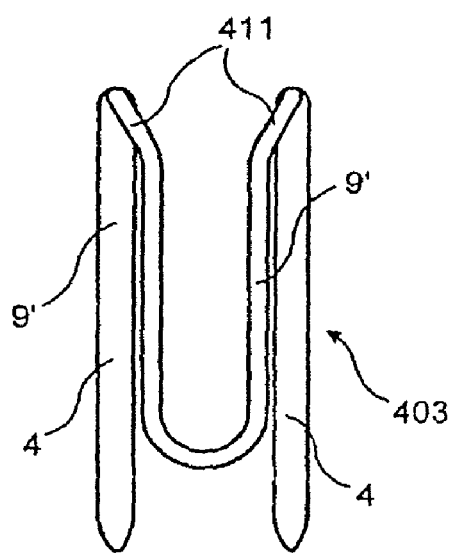
FIG. 28 is a plan view of a further embodiment according to the invention.
Figure 29:
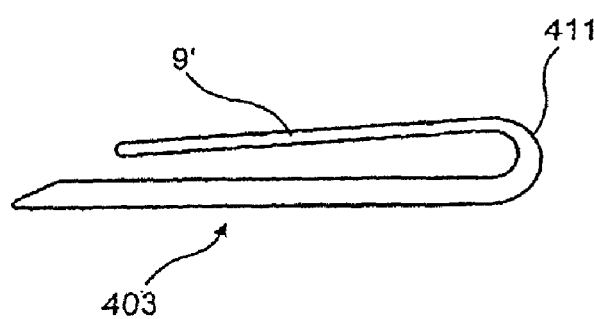
FIG. 29 is a side elevational view of the embodiment illustrated in FIG. 28.

FIGS. 28 and 29 show another embodiment 403 of the fixation device which is similar to the embodiment in FIG. 4A and the embodiment in FIGS. 26 and 27. The fixation embodiment 403 in FIGS. 28 and 29 is particularly adapted to fractures of the patella. The fixation device 403 differs from that in FIG. 4A in that bend portions 411 connecting the legs 4 and 9' are not in the same plane as the legs 9' so that the spacing between the opposite legs 9' is less than that between the opposite legs 4 as evident from FIG. 28. Additionally, the diameter of the legs 4 is greater than the diameter of the legs 9' and the change in diameter takes place gradually through the bend portions 411. Referring to FIGS. 30 and 31, therein the fixation device 403 is shown implanted in the patellar bone 2 across the fracture 2 in which two washers 15 and two bone screws 16 are employed.

Figure 32:
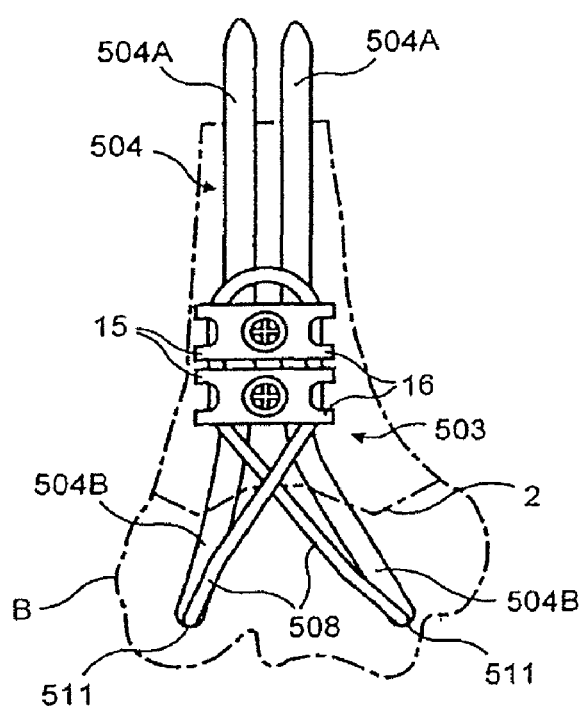
FIG. 32 shows a further embodiment of the invention installed in the bone.
Figure 33:
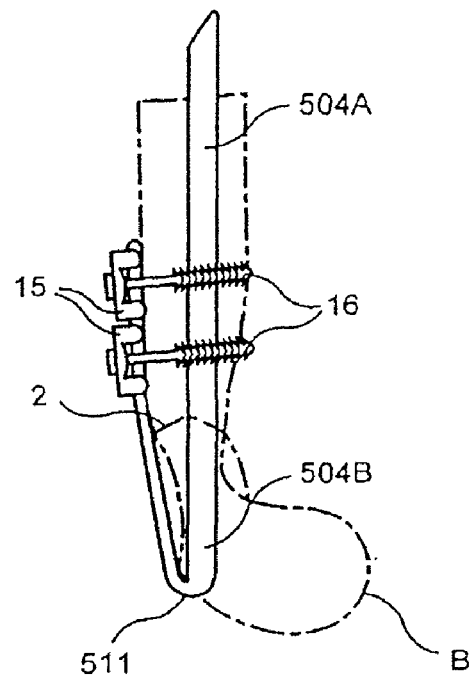
FIG. 33 is an elevational view of FIG. 32.

FIGS. 32 and 33 show another embodiment of the invention similar to the embodiment in FIG. 4 but modified to provide fixation for fractures of the proximal humerus, the distal humerus, the lateral humerus, the lateral malleolus and medial malleolus. The embodiment illustrated in FIGS. 32 and 33 and designated 504 differs from the earlier described embodiment of FIG. 4 in that legs 504 of the fixation device are not straight but are formed with straight portions 504A and diverging non-symmetrical portions 504B. The implant thereby is adapted to the configuration of the particular bone and the relatively wide aspect or spacing of the bend portions 511 as shown in FIG. 32. In this embodiment, two washers 15 and the bone screws 16 are utilized as in previous embodiments.

Figure 34:
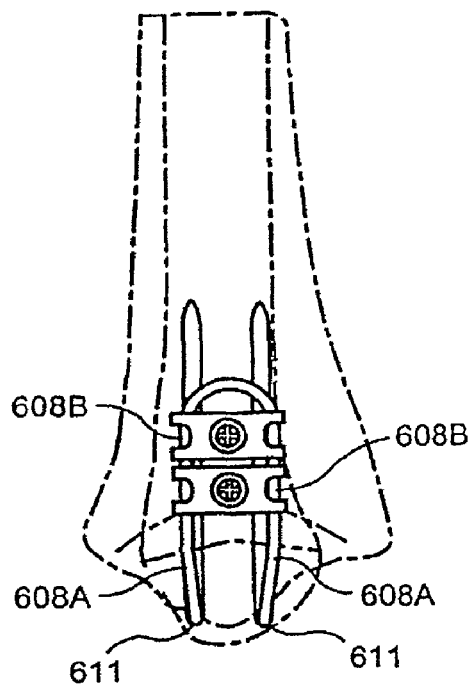
FIG. 34 shows a further embodiment installed in the bone.

FIG. 34 shows a variation of the embodiment in FIG. 32 adapted for being implanted in the medial malleolus. In this embodiment instead of the legs of the implanted first portion 5 being non-parallel, the legs 604 are parallel and the legs of the second portion are bent and widen from the bend portions 611 to form diverging leg portions 608A which merge with parallel leg portions 608B.

Figure 35:
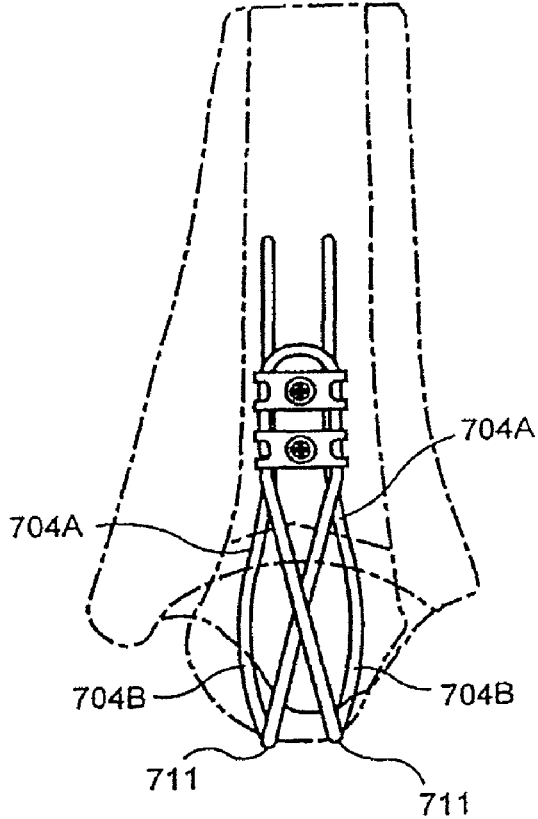
FIG. 35 is a plan view showing a further embodiment installed in the bone.

In a modification shown in FIG. 35, the legs of the first portion include diverging portions 704A which then converge to portions 704B which are joined to bend portions 711 connected to the crossing legs of the second portion of the fixation device.

FIGS. 36 and 37 show another embodiment of a fixation device 703 having a single straight leg 704 forming the first portion 705 of the fixation device connected by a bend portion 711 to a single leg 709 forming the second portion 708 of the fixation device. At the end of leg 709, a 90° bend is formed to define a hook 710.

In FIG. 38, the leg 704 of the fixation device is impacted into the intramedullary canal of the bone B across the fracture 2. An anchoring hole 712 is drilled in the bone B and is engaged by one arm 713 of a tensioning instrument 714. The other arm 715 engages the hook 710 at the end of leg 708. The tensioning instrument is then closed as shown in FIG. 39 to close and compress the fracture. A guide hole 715 is drilled in the bone B tensioning instrument 714 is then removed and hook 710 is impacted into the guide hole 715. A bone screw 716 and washer 717 is then installed to hold end of the leg 709 in place.

The embodiment shown in FIGS. 36-41 differs from the previously described embodiments in that instead of fixedly securing the end of leg 708 by the washer and bone screw, the hook which is impacted into the bone serves for anchoring the leg 708 and the bone screw and washer only serve for preventing the end of the leg from coming out of the bone. In the previously described embodiments the bone screw has to be tightened with substantial force to prevent the leg under the washer from sliding on the bone.

There will now be explained how the legs 4 are installed into bone B.

Figure 42:
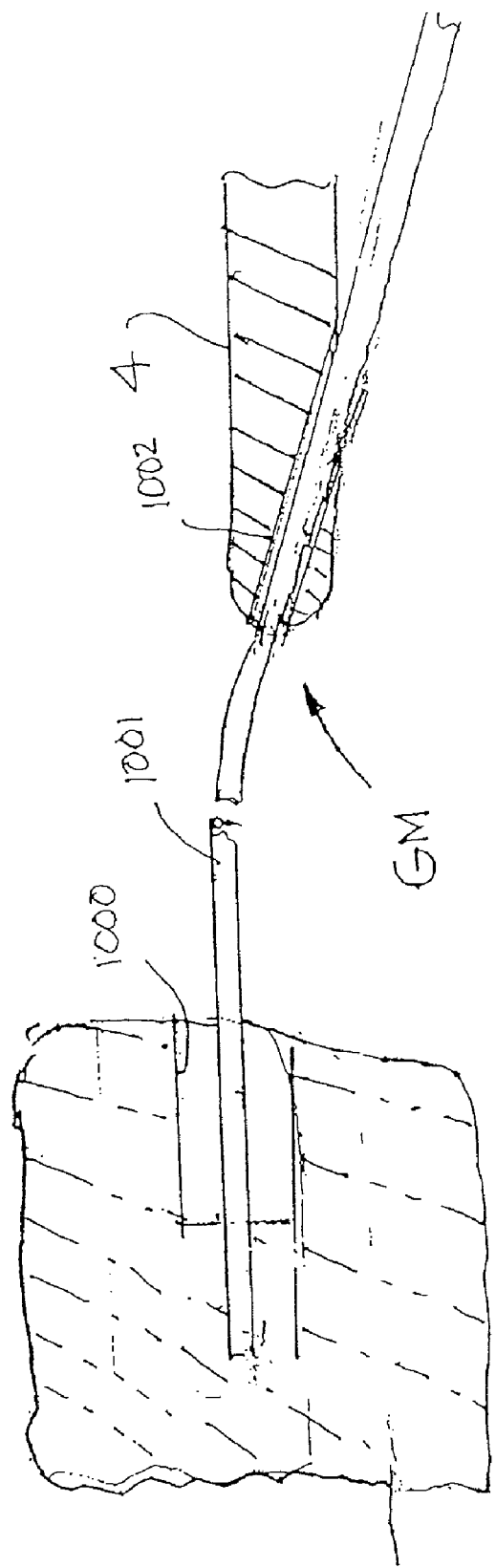
FIG. 42 is a diagrammatic sectional view on enlarged scale illustrating a guide means for installing the ends of legs of the implant device into pilot holes in bone.

Referring to FIG. 3 and the description thereof, in order to install the legs 4 into bone B, two pilot holes 1000 (FIG. 42) are first drilled into the bone B. The depth and diameter of the pilot holes 1000 are a function of the structure of the particular bone which is fractured and its quality (strength, hardness, elasticity etc.). In a first case, the pilot holes 1000 are approximately equal in diameter to the diameter of the legs 4 so that the legs 4 can be engaged in and supported by the pilot holes, preferably, with a frictional fit. The pilot holes 1000 are drilled to a depth that equals or exceeds the length of legs 4 and serve as a channel for insertion and support of the legs therein to enable tension to be developed in the wire element and compression to be applied across the fracture. Alternatively, the pilot holes may be drilled less than the length of legs 4 to serve as guide holes for entry of the legs into bone B after which the legs 4 are driven or impacted over the remaining distance into the bone much as a nail is driven into a piece of wood. In either case, feature of the invention is the manner in-which the legs 4 are inserted into the pilot holes 1000.

The insertion of the legs 4 into the pilot holes may be difficult under operating conditions and require some "hunting" on the part of the surgeon to insert the legs 4 into the guide holes, particularly when soft tissue and tendons obscure the small guide holes.

In order to facilitate installation of legs 4 into the pilot holes 1000 in bone B the invention provides a guide means GM connected between the bone B and legs 4 for guidable insertion of legs 4 into the pilot holes 1000.

The guide means GM is constituted by a guide wire in the form of a guide pin 1001 and a bore 1002 in the distal end of leg 4. In one embodiment, the bore 1002 is axially aligned with the predominant longitudinal axis of the leg and extends, from the tip of leg 4 along the length of leg 4 and exits in a region proximate to bend 7. In another preferred embodiment, the bore is directed at a specified angle to the predominant longitudinal axis of leg 4. Typical diameters for the guide pin 1001 range from 0.8 mm to 3 mm.

The bore 1002 is located proximate to the center of the tip of leg 4 to form an inlet end for guide pin 1001 and the bore 1002 extends obliquely downwards at an angle to exit at a bottom surface of leg 4 to form an outlet for guide pin 1001 (as explained later). In the preferred embodiment, the bore 1002 is angulated instead of extending longitudinally through leg 4 in order not to weaken the leg. The bore 1002 is slightly larger in diameter than the guide pin 1001 to allow the guide pin to be slidable in the bore 1002.

The operation of installing the legs 4 into the bone B is as follows.

The guide pins 1001 are drilled into bone B at the locations where legs 4 are to be installed in the bone. The pilot holes 1000 are then over drilled on the guide pins 1001 by a cannulated drill leaving the guide pins in the bone and extending from the pilot holes 1000. The guide pins 1001 are then inserted into bores 1002 in legs 4 and the free ends of guide pins 1001 extend out of the outlet ends of the bores 1002. The implant device is then slid along the guide pins until the tips of legs 4 enter the holes 1000 and the legs 4 are seated in the pilot holes 1000. The guide pins 1001 are then removed by pulling on the free ends of the guide pins extending out of legs 4. If the legs 4 are not fully seated in the pilot holes 1000 the legs 4 are then impacted into the bone B.

The guide pins thus serve as guides for insertion of the tips of legs 4 into the pilot holes 1000 in the bone and save a lot of time and frustration in hunting for the small holes 1000 in the bone during the operation, especially when the holes become covered by the somewhat elastic soft tissue after the pilot holes have been drilled.

Although the invention is disclosed with reference to particular embodiments thereof, it will become apparent to those skilled in the art that numerous modifications and variations can be made which will fall within the scope and spirit of the invention as defined by the attached claims.

The invention claimed is:

1. An implant for fixation of a bone fracture and for applying compression across the fracture, said implant comprising:
    a wire element having a first leg constructed and arranged to be implanted longitudinally in the bone and having a length to extend across the fracture and exit from the bone, and a second leg joined to the first leg by a bend, said bend having a size and shape so that the second leg extends linearly backwards in longitudinal juxtaposition with the first leg at a vertical spacing distance therefrom to overlie a superficial surface of the bone,
    guide means for guidable insertion of said first leg into a pilot hole in the bone and enable subsequent installation in the bone such that a longitudinal pulling force applied to the second leg will produce tension in the wire element and apply compression across the fracture, and
    means associated with said second leg and including a fixing element insertable in the bone for securing the second leg to the bone to maintain the tension developed in the wire element and continue to apply the compression across the fracture, wherein said guide means comprises a guide wire adapted to be secured in the bone and a bore in said first leg into which said guide wire is insertable, said guide wire having a length to extend through the bone and exit from the bore wherein said guide wire and said bore are sized to permit said first leg to be slid along the guide wire to be inserted into said pilot hole in the bone wherein said guide wire is secured in the bone at a rear wall of the pilot hole and said guide wire extends through the pilot hole to exit from the pilot hole and the bone.

2. The implant as claimed in claim 1, wherein said bore is angulated in said first leg, said bore having an inlet opening at a tip end of said first leg and an outlet opening at a side of said first leg.

3. The implant as claimed in claim 2, wherein said guide wire and said bore are sized to permit said first leg to be slid along the guide wire to be inserted into said pilot hole in the bone.

4. The implant as claimed in claim 1, wherein said guide wire has a length to extend from the outlet opening in the first leg when the first leg is inserted in the pilot hole in the bone.

5. The implant as claimed in claim 4, wherein said guide wire is removable from the bone when the first leg has been inserted into the pilot hole in the bone.

6. The implant as claimed in claim 1, wherein said wire element has a pair of said first legs and respective said guide means connecting the bone and each said first leg.

7. The implant as claimed in claim 1, wherein guide wire comprises a guide pin.

8. The implant as claimed in claim 1, wherein said guide wire is driven into the bone and said pilot hole is formed around said guide wire by overdrilling the bone.

9. A method for fixation of a bone fracture comprising the steps of:
   providing a wire element having first and second legs joined by a bend, said first leg having a bore extending therethrough,
   securing the first leg into a fractured bone so that the first leg extends across the fracture and exits from the bone to join the bend and cause the second leg to extend backwardly over a posterior surface of the bone,
   applying a pulling force on the second leg to develop tension in the wire element and produce compression across the fracture, and
   securing the second leg to the bone to maintain the tension in the wire element and the compression across the fracture;
   said step of securing the first leg into the fractured bone comprising:
      installing a guide wire in the bone at a location at which the first leg is to be secured in the bone;
      forming a pilot hole in the bone around the guide wire;
      inserting the guide wire through the bore in the first leg to extend outwards thereof; and
      sliding said wire element along the guide wire and cause a tip of the first leg to guidably enter the pilot hole.

10. The method as claimed in claim 9, comprising removing said guide wire from the bone after the first leg, has been inserted into the pilot hole, by pulling the guide wire extending from the first leg.

11. The method as claimed in claim 9, wherein the guide wire is secured in the bone by drilling the guide wire into the bone and thereafter the pilot hole is formed in the bone by overdrilling the guide wire.

12. The method as claimed in claim 9, wherein the guide hole in the first leg is sized to enable sliding of the first leg along the guide wire.

13. The method as claimed in claim 9, comprising forming said guide wire as a guide pin.

14. The method as claimed in claim 9, comprising forming said bore in said first leg at an angle relative to a longitudinal axis of said first leg so that the guide wire exits from said first leg at a side thereof.

\* \* \* \* \*